United States Patent
Dickie

(10) Patent No.: US 11,683,829 B2
(45) Date of Patent: Jun. 20, 2023

(54) SYSTEMS AND METHODS FOR IMPROVING QUALITY OF SERVICE WHEN TRANSMITTING ULTRASOUND IMAGE DATA OVER A WIRELESS CONNECTION

(71) Applicant: Clarius Mobile Health Corp., Vancouver (CA)

(72) Inventor: Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 121 days.

(21) Appl. No.: 17/335,070

(22) Filed: May 31, 2021

(65) Prior Publication Data

US 2022/0386313 A1 Dec. 1, 2022

(51) Int. Cl.
| | | |
|---|---|---|
| H04L 12/28 | (2006.01) | |
| H04W 72/542 | (2023.01) | |
| A61B 8/00 | (2006.01) | |
| H04W 24/08 | (2009.01) | |
| H04W 72/0453 | (2023.01) | |
| H04J 1/16 | (2006.01) | |

(52) U.S. Cl.
CPC ......... *H04W 72/542* (2023.01); *A61B 8/4472* (2013.01); *A61B 8/461* (2013.01); *A61B 8/565* (2013.01); *H04W 24/08* (2013.01); *H04W 72/0453* (2013.01)

(58) Field of Classification Search
CPC ....... G01S 3/80; H04M 7/006; H04W 72/085; H04W 84/12; H04W 24/08; H04W 72/542; H04W 72/0453; A61B 8/565
USPC ................ 370/252, 329, 386, 430
See application file for complete search history.

(56) References Cited

U.S. PATENT DOCUMENTS

| | | | |
|---|---|---|---|
| 9,649,091 B2 | 5/2017 | Halmann | |
| 2005/0251040 A1* | 11/2005 | Relkuntwar | A61B 8/4411 600/437 |
| 2007/0239001 A1* | 10/2007 | Mehi | G01S 7/52095 600/437 |
| 2008/0037880 A1* | 2/2008 | Lai | H04N 19/64 375/240 |
| 2016/0249874 A1* | 9/2016 | Korporaal | A61B 6/0487 382/131 |
| 2017/0086798 A1 | 3/2017 | Bjaerum et al. | |

\* cited by examiner

*Primary Examiner* — John Pezzlo
(74) *Attorney, Agent, or Firm* — Julian Ho; Susan Ben-Oliel

(57) ABSTRACT

The present embodiments relate generally to systems and methods for ultrasound imaging. The methods may involve: establishing a wireless network between an ultrasound imaging device and a display device; acquiring ultrasound image data using ultrasound acquisition parameters; transmitting the ultrasound image data from the ultrasound imaging device to the display device over the wireless network; receiving the ultrasound image data; measuring a quality of service parameter of the received ultrasound image data; determining whether the measured quality of service parameter is less than an expected quality of service parameter, the expected quality of service parameter being determined based on the ultrasound acquisition parameters used to acquire the ultrasound image data; and in response to determining that the measured quality of service parameter is less than the expected quality of service parameter, adjusting a network parameter of the wireless network to reduce network traffic on the wireless network.

16 Claims, 7 Drawing Sheets

SYSTEMS AND METHODS FOR IMPROVING QUALITY OF SERVICE WHEN TRANSMITTING ULTRASOUND IMAGE DATA OVER A WIRELESS CONNECTION

FIELD

The present disclosure relates generally to ultrasound imaging, and in particular, systems and methods for improving quality of service (QoS) when transmitting ultrasound image data over a wireless connection.

BACKGROUND

Ultrasound imaging systems are an important tool for diagnosis and therapy in a wide range of medical applications. Conventionally, ultrasound systems were large, expensive units used only in radiology departments by highly trained specialists. To improve portability and usability and enable ultrasound to be used at the point-of-care and by more users, various attempts have been made to reduce the size and cost of these systems and avoid the ergonomically troublesome cables that are typically used to attach handheld transducers to processing hardware. For example, one handheld medical diagnostic ultrasound imaging system wirelessly communicates ultrasound data to a multi-use display device such as a commercially available PDA or tablet computer.

In addition to size and cost, wireless ultrasound systems may also face challenges related to network quality. In wireless ultrasound systems, the quality of the wireless network can affect the transmission of image data, and therefore affect the viewing experience for the operator at the display device. For example, poor wireless network quality may limit data bandwidth, which may result in latency or dropped frames at the display device. Many factors can affect wireless network quality, including, for example, environmental conditions, network traffic, and the like. It may be difficult for an operator to determine how to improve network quality during an ultrasound imaging procedure. For instance, the operator may lack the technical expertise required to troubleshoot a wireless network. Furthermore, even if the operator could correctly identify issues with the wireless network, the operator may not have sufficient time to address the network issues during an imaging procedure, especially in time-critical applications, such as emergency medicine.

There is thus a need for improved ultrasound imaging systems and methods that automatically enhance QoS when transmitting of ultrasound image data over a wireless connection. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
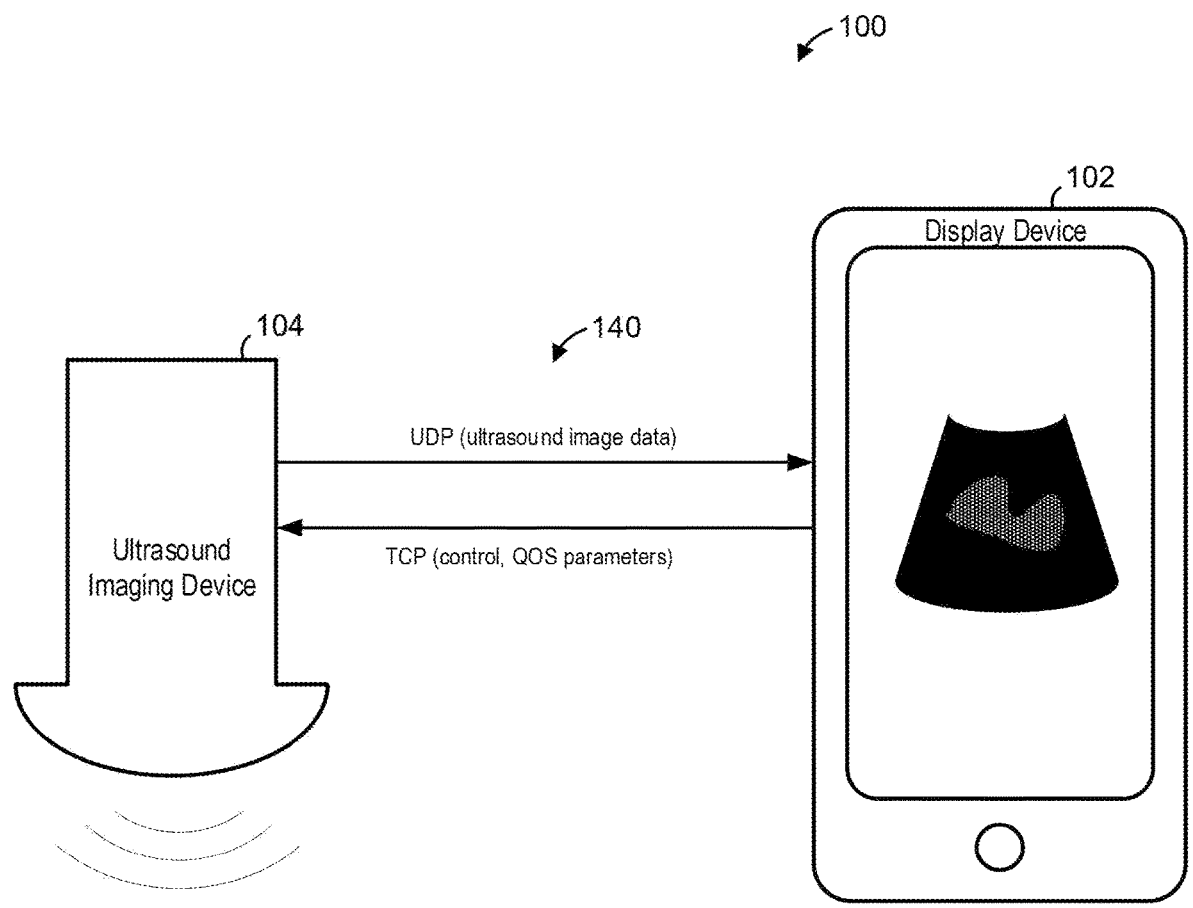
FIG. 1 is a block diagram of an example ultrasound imaging system, in accordance with at least one embodiment of the present invention.

In a broad aspect of the present disclosure, there is provided a method for ultrasound imaging. The method involves: establishing a wireless network between an ultrasound imaging device and a display device; acquiring ultrasound image data at the ultrasound imaging device using ultrasound acquisition parameters; transmitting the ultrasound image data from the ultrasound imaging device to the display device over the wireless network; receiving the ultrasound image data at the display device; measuring, at the display device, a quality of service parameter of the received ultrasound image data; determining, at at least one of the display device and the ultrasound imaging device, whether the measured quality of service parameter is less than an expected quality of service parameter, the expected quality of service parameter being determined based on the ultrasound acquisition parameters used to acquire the ultrasound image data at the ultrasound imaging device; and in response to determining that the measured quality of service parameter is less than the expected quality of service parameter, adjusting a network parameter of the wireless network to reduce network traffic on the wireless network.

In some embodiments, the measured quality of service parameter may include a displayed frame rate of the received ultrasound image data, and the expected quality of service parameter may include an acquisition frame rate at the ultrasound imaging device.

In some embodiments, the adjusting the network parameter may involve switching the wireless network to a different band.

In some embodiments, the adjusting the network parameter may involve switching the wireless network to a different channel within the same frequency band.

In some embodiments, the switching the wireless network to a different channel may involve: scanning a plurality of channels within the frequency band to determine an amount of network traffic present on each channel; and switching the wireless network to the channel having the least amount of network traffic.

In some embodiments, in response to the determining that the measured quality of service parameter is less than the expected quality of service parameter, the method may further involve adjusting at least one ultrasound acquisition parameter of the ultrasound acquisition parameters used at the ultrasound imaging device, the adjusting being performed to reduce the data size of subsequent ultrasound image data acquired by the ultrasound imaging device.

In some embodiments, the adjusted at least one ultrasound acquisition parameter may include: acquisition frame rate, sampling rate, line density or sampling frequency.

In some embodiments, prior to the determining, whether the measured quality of service parameter is less than the expected quality of service parameter, the method may further involve: determining the expected quality of service parameter at the ultrasound imaging device; and transmitting the expected quality of service parameter from the ultrasound imaging device to the display device.

In some embodiments, the wireless network may be hosted by the ultrasound imaging device, and the method may further involve transmitting the measured quality of service parameter from the display device to the ultrasound imaging device over the wireless network.

In some embodiments, the ultrasound image data may be transmitted over the wireless network using a first communication protocol; and the measured quality of service parameter may be transmitted over the wireless network using a second communication protocol that is different from the first communication protocol.

In some embodiments, the first communication protocol may include User Datagram Protocol (UDP) and the second communication protocol may include Transmission Control Protocol (TCP).

In some embodiments, the wireless network may be a Wi-Fi™ network.

In another broad aspect of the present disclosure, there is provided a system for ultrasound imaging. The system includes an ultrasound imaging device and a display device in electronic communication with the ultrasound imaging device over a wireless network. The ultrasound imaging device is configured to acquire ultrasound image data using ultrasound acquisition parameters. The display device is configured to: receive the ultrasound image data from the ultrasound imaging device over the wireless network; and measure a quality of service parameter of the received ultrasound image data. At least one of the display device and the ultrasound imaging device is configured to: determine whether the measured quality of service parameter is less than an expected quality of service parameter, the expected quality of service parameter being determined based on the ultrasound acquisition parameters used to acquire the ultrasound image data at the ultrasound imaging device; and in response to determining that the measured quality of service parameter is less than the expected quality of service parameter, adjusting a network parameter of the wireless network to reduce network traffic on the wireless network.

In some embodiments, the measured quality of service parameter may include a displayed frame rate of the received ultrasound image data, and the expected quality of service parameter may include an acquisition frame rate at the ultrasound imaging device.

In some embodiments, the adjusting the network parameter may involve switching the wireless network to a different band.

In some embodiments, the adjusting the network parameter may involve switching the wireless network to a different channel within the same frequency band.

In some embodiments, the switching the wireless network to a different channel may involve: scanning a plurality of channels within the frequency band to determine an amount of network traffic present on each channel; and switching the wireless network to the channel having the least amount of network traffic.

In some embodiments, at least one of the display device and the ultrasound imaging device may be further configured to: in response to the determining that the measured quality of service parameter is less than the expected quality of service parameter, adjust at least one ultrasound acquisition parameter of the ultrasound acquisition parameters used at the ultrasound imaging device, the adjusting being performed to reduce the data size of subsequent ultrasound image data acquired by the ultrasound imaging device.

In some embodiments, the adjusted at least one ultrasound acquisition parameter may include: acquisition frame rate, sampling rate, line density or sampling frequency.

In some embodiments, the ultrasound imaging device may be further configured to: prior to the determining whether the measured quality of service parameter is less than the expected quality of service parameter, determine the expected quality of service parameter; and transmit the expected quality of service parameter to the display device.

In some embodiments, the wireless network may be hosted by the ultrasound imaging device, and the display device may be further configured to: transmit the measured quality of service parameter to the ultrasound imaging device over the wireless network.

In some embodiments, the ultrasound image data may be transmitted over the wireless network using a first communication protocol; and the measured quality of service parameter may be transmitted over the wireless network using a second communication protocol that is different from the first communication protocol.

In some embodiments, the first communication protocol may include User Datagram Protocol (UDP) and the second communication protocol may include Transmission Control Protocol (TCP).

In some embodiments, the wireless network may be a Wi-Fi™ network.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a block diagram of an example system for ultrasound imaging, in accordance with at least one embodiment of the present invention. As shown, the ultrasound imaging system 100 can include a display device 102 and an ultrasound imaging device 104.

The ultrasound imaging device 104 is generally operable to acquire ultrasound image data. The ultrasound imaging device 104 can be any suitable ultrasound probe or scanner. In some embodiments, the ultrasound imaging device 104 is a handheld device. To acquire the ultrasound image data, the ultrasound imaging device 104 can transmit ultrasound energy to a target object, receive ultrasound energy reflected from the target object, and generate ultrasound image data based on the reflected ultrasound data. For example, the ultrasound imaging device 104 may include a transducer that converts electric current into ultrasound energy and vice versa. The transducer may transmit ultrasound energy to a target issue, which echoes off the tissue. The echoes may be detected by a sensor in the transducer and relayed through suitable electronics.

The ultrasound imaging device 104 can acquire the ultrasound image data using various ultrasound acquisition parameters. For example, the ultrasound acquisition parameters may include an acquisition frame rate, a sampling frequency, and/or a line density. The acquisition frame rate can define the number of frames per second acquired by the ultrasound imaging device 104. The sampling frequency can define the number of samples per scan line in each frame (e.g., the axial resolution). The line density can define the number of scan lines in each frame (e.g., the lateral resolution). The ultrasound acquisition parameters can be adjusted to adjust the size of the ultrasound image data generated by the ultrasound imaging device 104. For example, increasing the acquisition frame rate, sampling frequency, and/or line density can increase the size of the ultrasound image data, whereas decreasing the acquisition frame rate, sampling frequency, and/or line density can decrease the size of the ultrasound image data.

The ultrasound imaging device 104 can be in electronic communication with the display device 102 through a wireless network 140. The wireless network 140 can be any suitable wireless network. In some embodiments, the wireless network 140 may be a Wi-Fi™ network. In some embodiments, the wireless network 140 can be initially provisioned using a separate data connection. For example, various information for establishing a Wi-Fi™ network can be initially exchanged between the display device 102 and the ultrasound imaging device 104 using a Bluetooth™ connection, as described in the Applicant's issued patent U.S. Pat. No. 9,763,644 B2, issued Sep. 19, 2017, the entire contents of which are hereby incorporated by reference.

The wireless network 140 can be hosted by the ultrasound imaging device 104 or the display device 102. In some embodiments, the wireless network 140 is hosted by the ultrasound imaging device 104. For example, the ultrasound imaging device 104 can use Wi-Fi Direct™ to provide a local hotspot that the display device 102 can connect to using a built-in Wi-Fi™ network interface on the display device 102. In other embodiments, the wireless network 140 can be hosted by a separate wireless router (e.g., as described herein with regard to FIGS. 6 and 7).

In operation, the ultrasound imaging device 104 can transmit ultrasound image data to the display device 102 through the wireless network 140. As shown, the ultrasound image data can be transmitted from the ultrasound imaging device 104 to the display device 102 using User Datagram Protocol (UDP). UDP has less overhead because it does not guarantee successful transmission of data. UDP can thus provide relatively fast transmission speeds (faster than Transmission Control Protocol (TCP), for example). However, some frames of the ultrasound image data may be dropped or otherwise not received by the display device 102. If the frame rate when transmitting ultrasound image data is sufficiently high (e.g., 15-30 frames pers second), occasional dropped frames may not be detectable by an operator.

In various embodiments, the display device 102 may be configured to periodically send pings via TCP to the ultrasound imaging device 104 to maintain the wireless network connection 140 between the ultrasound imaging device 104 and the display device 102. If the ultrasound imaging device 104 misses a periodic ping from the display device 102, it may stop imaging because the ultrasound imaging device 102 may no longer be within the vicinity of the display device 102 or because the network congestion may be so poor that no ultrasound imaging data is effectively being received at the display device 102. Stopping imaging in this manner may also align with ALARA ("as low as reasonably achievable") principles to reduce the ultrasound energy directed at a patient. It may also help the ultrasound imaging device 104 to reduce unnecessary power consumption.

In various embodiments, the ultrasound image data may be transmitted in various formats, including uncompressed and compressed formats, and may include various pre-scan, post-scan, greyscale, and/or RGB (red, green, blue) data.

In various embodiments, if compressed formats are used, compression could be lossless or lossy. If lossy compression is used, the compression quality percentage may be adjusted in view of network performance on wireless network 140. For example, the compression quality percentage may be the quality percentage when the Joint Photographic Experts Group (JPEG) algorithm is used. Additionally or alternatively, the type of compression used may be Portable Network Graphics (PNG) and/or Moving Picture Experts Group (MPEG) (e.g., if compression is being performed over ultrasound media that has multiple frames such as a cineloop). The adjustment of compression quality percentage may be additional or alternative to the adjusting of network parameters and/or ultrasound acquisition parameters discussed elsewhere herein.

In some embodiments, speckle reduction may be performed on the ultrasound image data prior to being compressed for transmission over the wireless network 140. The intensity of the speckle reduction may be controlled to maintain the compressed, speckled-reduced ultrasound image below an available bandwidth on the wireless network 140. Further details for how speckle reduction can be adjusted in view of available bandwidth on the wireless network 140 are discussed in Applicant's issued U.S. Pat. No. 10,405,836 B2 issued on Sep. 10, 2019, the entire contents of which are hereby incorporated by reference.

Referring still to FIG. 1, the display device 102 may generally be operable to receive the ultrasound image data from the ultrasound imaging device 104 through the wireless network 140. The display device 102 can be any suitable any suitable electronic device incorporating a display and a processor, such as a mobile device (e.g., smartphone), tablet, laptop, smartwatch, and the like. The display device 102 can display the received ultrasound image data so that an operator can view the ultrasound image data on the display device 102.

The display device 102 can measure a QoS parameter of the ultrasound image data received from the ultrasound imaging device 104. As will be understood, QoS in the context of computer networking refers to the performance perceived by the users. For example, QoS can be impacted by several related aspects of the network service, such as packet loss, bit rate, throughput, transmission delay, and availability. In some embodiments, the QoS parameter measured at the display device 102 may include a displayed frame rate and/or a received frame rate. The displayed frame rate may indicate the number of frames per second of the ultrasound image data displayed at the display device 102. The received frame rate may indicate the number of frames per second of the ultrasound image data received at the display device 102. The displayed/received frame rate can vary as the quality or performance of the wireless network 140 changes. For example, the displayed/received frame rate can decrease as network quality degrades and an increasing number of frames are dropped. Correspondingly, the displayed/received frame rate can increase as network quality improves and as fewer frames are dropped. As discussed in greater detail below, the QoS parameter measured at the display device 102 can be compared to an expected QoS parameter, and the result of this comparison can be used to determine whether to adjust network parameters of the wireless network 140 and/or ultrasound acquisition parameters of the ultrasound imaging device 104.

The display device 102 can transmit various control instructions to the ultrasound imaging device 104 through the wireless network 140. For example, the control instructions may include commands to adjust one or more ultrasound acquisition parameters of the ultrasound imaging device 104. Additionally or alternatively, when the wireless network 140 is hosted by the ultrasound imaging device 104, the display device 102 may transmit commands to adjust one or more network parameters of the wireless network 140. In various embodiments, the control instructions may be generated automatically by the display device 102, and/or in response to input received from an operator of the ultrasound system. The display device 102 may also transmit various other data to the ultrasound imaging device 104 through the wireless network 140. For example, the display device 102 may transmit a measured QoS parameter to the ultrasound imaging device 104.

Control and other data can be transmitted by the display device 102 to the ultrasound imaging device 104 using a different transmission protocol than was used by the ultrasound imaging device 104 to transmit ultrasound image data to the display device 102. For example, as shown in FIG. 1, control and other data may be transmitted using Transmission Control Protocol (TCP). In contrast to UDP, TCP has extra overhead to guarantee successful transmission of data. This may result in transmission speeds that are relatively slower than UDP. However, the use of TCP may ensure that important messages, such as control instructions and measured QoS parameters, are successfully delivered to the ultrasound imaging device 104. In various embodiments, the display device 102 may not transmit the measured quality of service parameter to the ultrasound imaging device 104, for example, when the wireless network 140 is hosted by the display device 102.

Figure 2:
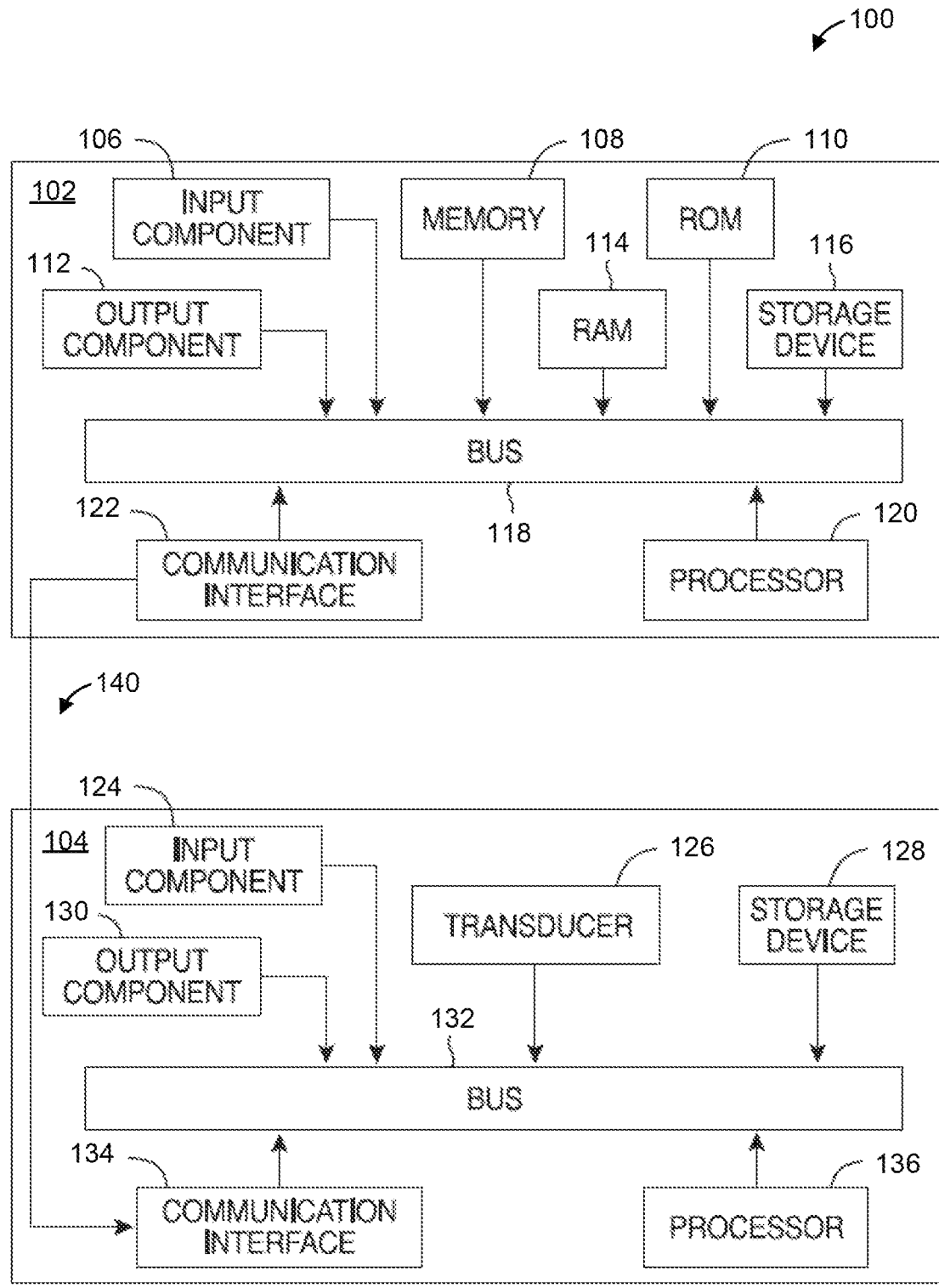
FIG. 2 is another block diagram of the ultrasound imaging system shown in FIG. 1 illustrating various subcomponents in additional detail, in accordance with at least one embodiment of the present invention.

Referring now to FIG. 2, there is shown another block diagram of the ultrasound imaging system 100, illustrating various subcomponents in additional detail, in accordance with at least one embodiment of the present invention.

As described herein, ultrasound imaging device 104 is generally configured to transmit ultrasound energy to a target object, receive ultrasound energy reflected from the target object, and generate ultrasound image data based on the reflected ultrasound energy. Ultrasound imaging device 104 may include a transducer 126 which converts electric current into ultrasound energy and vice versa. Transducer 126 may transmit ultrasound energy to the target object which echoes off the tissue. The echoes may be detected by a sensor in transducer 126 and relayed through a bus 132 to a processor 136. Processor 136 may interpret and process the echoes to generate image data of the scanned tissue. In some embodiments, the ultrasound imaging device 104 (or various components thereof) may be provided as a handheld ultrasound probe that is in communication with other components of the ultrasound imaging system 100. For example, the handheld probe may include the transducer 126 of ultrasound imaging device 104. Ultrasound imaging device 104 may also include storage device 128 (coupled to and accessible by bus 132) for storing software or firmware instructions, configuration settings (e.g., sequence tables), and/or ultrasound image data.

Although not illustrated, the ultrasound imaging device 104 may include other components for acquiring, processing and/or displaying ultrasound image data. These include, but are not limited to: a scan generator, transmit beamformer, pulse generator, amplifier, analogue to digital converter (ADC), receive beamformer, signal processor, data compressor, wireless transceiver and/or image processor. Each of these may be components of ultrasound imaging device 104 and/or display device 102.

The display device 102 can be in communication with ultrasound imaging device 104 via communication interfaces 122/134. In various embodiments, communication interfaces 122/134 may allow for wired or wireless connectivity (e.g., via Wi-Fi™ and/or Bluetooth™ as discussed above with respect to FIG. 1) between the display device 102 and the ultrasound imaging device 104. Display device 102 may work in conjunction with ultrasound imaging device 104 to control the operation of ultrasound imaging device 104 and display the images acquired by the ultrasound imaging device 104. An ultrasound operator may interact with the user interface provided by display device 102 to send control commands to the ultrasound imaging device 104 to adjust various parameters discussed herein. The display device 102 may be a portable device, which may include a mobile device (e.g., smartphone), tablet, laptop, or other suitable device incorporating a display and a processor and capable of accepting input from a user and processing and relaying the input to control the operation of the ultrasound imaging device 104 as described herein.

Each of ultrasound imaging device 104 and display device 102 may have one or more input components 124, 106 and/or one or more output components 130, 112. In the FIG. 2 embodiment, ultrasound imaging device 104 may include an input component 124 which is configured to accept input from the user (e.g., to turn on the ultrasound imaging device 104, adjust settings on the ultrasound imaging device 104, and/or control the connection of the ultrasound imaging device 104 to the display device 102). For example, in some embodiments, ultrasound imaging device 104 may also include an output component 130, such as a LED indicator light which can output the status of the ultrasound imaging device 104.

In the example embodiment of FIG. 2, display device 102 may include an input component 106 configured to accept input from the user. Certain input received at input component 106 may be relayed to ultrasound imaging device 104 to control the operation of ultrasound imaging device 104. Display device 102 may also include an output component 112, such as a display screen, which displays images based on image data acquired by ultrasound imaging device 104. In particular embodiments, input component 106 may include a touch interface layered on top of the display screen of the output component 112.

Display device 102 may also include memory 108, Random Access Memory (RAM) 114, Read Only Memory (ROM) 110, and persistent storage device 116, which may all be connected to bus 118 to allow for communication therebetween and with processor 120. Ultrasound imaging device 104 may contain memory (e.g., storage device 128) that may be accessible by processor 136. Any number of these memory elements may store software or firmware that may be accessed and executed by processor 120 and/or processor 136 to, in part or in whole, perform the acts of the methods described herein.

In some embodiments, all of the input controls and display screen necessary for the operation of the ultrasound imaging system 100 may be provided by input and output components 106, 112 of the display device 102. In such cases input and output components 124, 130 of ultrasound imaging device 104 may be optional and/or omitted. In certain embodiments, the ultrasound imaging device 104 may be a handheld probe (e.g., including transducer 126) which is in communication with the display device 102 over the communications interfaces 122/134 to facilitate operation of the ultrasound imaging device 104 and processing and display of ultrasound images.

In various embodiments, at least a portion of the processing of the image data corresponding to the reflected ultrasound energy detected by the handheld probe's transducer 126 may be performed by one or more of processors internal to the ultrasound imaging device 104 (such as by the processor 136) and/or by processors external to the ultrasound imaging device 104 (such as the processor 120 of display device 102). By having some of the image data processing tasks typically performed by a processor 136 of ultrasound imaging device 104 be performed instead by a processor 120 of the display device 102, less physical processing hardware may need to be provided on the ultrasound imaging device 104. This may facilitate a lightweight, portable design and construction for the ultrasound imaging device 104 (e.g., when it is a handheld probe). In particular embodiments, the handheld probe may have a mass that is less than approximately 1 kg (2 lbs).

In some embodiments, the output component 130 of ultrasound imaging device 104 may include a display screen, which can be configured to display or otherwise output the images acquired by ultrasound imaging device 104 (in addition to or alternative to displaying such images on the display device 102).

Figure 3:
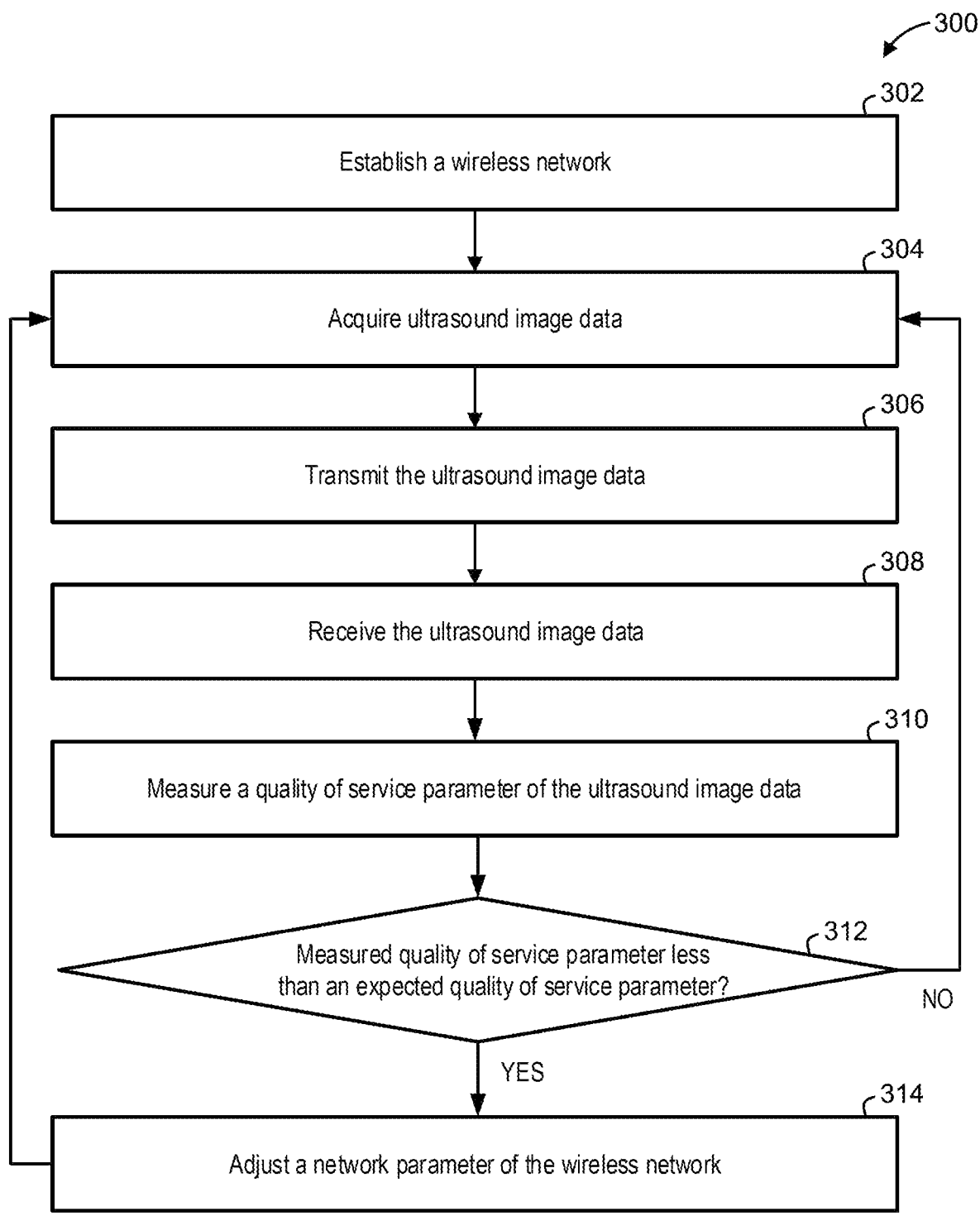
FIG. 3 is a flowchart diagram of an example method for operating the ultrasound imaging system shown in FIGS. 1 and 2, in accordance with at least one embodiment of the present invention.

Referring now to FIG. 3, shown there generally as 300 is a block diagram of an example method for ultrasound imaging, in accordance with at least one embodiment of the present invention. An example implementation of the ultrasound imaging method 300 will now be described with reference to the ultrasound imaging system 100 shown in FIGS. 1 and 2.

At 302, the wireless network 140 may be established between the ultrasound imaging device 104 and the display device 102. As described herein, the wireless network 140 can be hosted by the ultrasound imaging device 104 or the display device 102. For example, the wireless network 140 may be hosted at the ultrasound imaging device 104 as a Wi-Fi Direct™ hotspot that can be connected to by the display device 102. In some embodiments, as noted above, the connection details for the wireless network 140 may be a Wi-Fi™ network that is initially provisioned using a Bluetooth™ connection.

At 304, the ultrasound imaging device 104 may acquire ultrasound image data using ultrasound acquisition parameters. For example, this may include operating the ultrasound imaging device 104 on a patient to image tissue of the patient. There may be various acquisition parameters involved in acquiring ultrasound image data. As noted above, the ultrasound acquisition parameters that the ultrasound imaging device 104 uses when may include an acquisition frame rate (e.g., a number of frames per second), a sampling frequency (e.g., a number of samples per scan line in each frame), and/or a line density (e.g., a number of scan lines in each frame).

At 306, the ultrasound imaging device 104 may transmit the acquired ultrasound image data to the display device 102 through the wireless network 104. As noted above, the ultrasound image data may be transmitted from the ultrasound imaging device 104 to the display device 102 using User Datagram Protocol (UDP).

In various embodiments, the ultrasound image data may be transmitted in various formats. For example, the ultrasound image data may be transmitted in pre-scan converted format or post-scan converted format. Scan conversion refers to the construction of an ultrasound media, such as a still image or a video, from lines of ultrasound scan data representing echoes of ultrasound signals. Scan conversion may involve converting pre-scan converted data (e.g., beams and/or vectors of acoustic scan data which are in polar (R-theta) coordinates) to post scan converted image data (e.g., which may be in cartesian (x-y) coordinates). The ultrasound image data transmitted from the ultrasound imaging device 104 to the display device 102 may be in either format.

Additionally or alternatively, as noted above, the transmitted ultrasound imaging data may be compressed according to various compression protocols to reduce the size of the ultrasound image data transmitted.

At 308, the display device 102 may receive the ultrasound image data from the ultrasound imaging device 104 through the wireless network 140. Since the ultrasound image data is being transmitted through a wireless network 140, the quality of the network connection between the ultrasound imaging device 104 and the display device 102 may not always be good. For example, if the system is operating in an environment where there are many other available wireless networks (e.g., in an education setting where there are many wireless ultrasound imaging devices 104 operating at the same time), the throughput of the received ultrasound image data at display device 102 may be low.

At 310, the display device 102 may measure a QoS parameter of the received ultrasound image data. The measured QoS parameter may be any parameter that indicates performance of the wireless network 140. For example, as noted, the QoS parameter may include a displayed frame rate (e.g., a number of frames per second of the ultrasound image data displayed at the display device 102) and/or a received frame rate (e.g., a number of frames per second of the ultrasound image data received at the display device 102).

At 312, at least one of the display device 102 or the ultrasound imaging device 104 determines whether the measured QoS parameter is less than an expected QoS parameter. The display device may generally monitor the QoS parameter as the ultrasound imaging device (e.g., the transmitting probe) may not know how much of the ultrasound stream (e.g., transmitted via UDP protocol) made it across. When comparing the measured the QoS parameter to the expected QoS parameter, in embodiments where this comparison is performed at the ultrasound imaging device 104, the display device 104 may send QoS parameters back to the ultrasound imaging device 104 using TCP protocol to ensure delivery. The ultrasound imaging device 104 may then be made aware about the QoS parameter and can make the comparison at 312.

In some embodiments, the expected QoS parameter may be determined based on the ultrasound acquisition parameters, such as the acquisition frame rate, sampling frequency, and/or a line density. For example, the expected QoS parameter may be an acquisition frame rate at the ultrasound imaging device 104 (e.g., the number of frames per second acquired at the display device 102). The expected QoS parameter can generally indicate the expected value of the measured QoS parameter under ideal network conditions. For example, under ideal network conditions, the expected displayed/received frame rate at the display device 102 would be expected to match the acquisition frame rate at the ultrasound imaging device 104 since there should be no loss of frames when the ultrasound image data is transmitted over the wireless network 140.

In some embodiments, the expected QoS parameter may be determined at the ultrasound imaging device 104 or the display device 102. For example, the expected QoS parameter may be determined at the ultrasound imaging device 104 and transmitted to the display device 102 (e.g., via TCP protocol to ensure delivery) so that act 312 can be performed at the display device 102 to compare the measured QoS parameter against the expected QoS parameter. Additionally or alternatively, the ultrasound acquisition parameters used to acquire the ultrasound image data at 304 can be transmitted to the display device 102, and the display device 102 can calculate the expected QoS parameter based on the ultrasound acquisition parameters. For example, if the QoS parameter is the frame rate, the sampling frequency and line density at the ultrasound imaging device 104 can be transmitted to the display device 102, and the display device 102 can calculate the expected frame rate based on these ultrasound acquisition parameters. In this case, the comparison at 312 may be performed at the display device 102.

As shown in FIG. 3, if the measured QoS parameter is less than the expected QoS parameter (indicating poor network performance in the wireless network 140), the method 300 proceeds to 314. Otherwise, if the measured QoS parameter matches or exceeds the expected QoS parameter, the method 300 proceeds back to 304 and image acquisition continues.

At 314, a network parameter of the wireless network 140 may be adjusted to improve network traffic flow on the wireless network 140. The network parameter may be adjusted in response to determining that the measured quality of service parameter is less than the expected quality of service parameter at 312. In other words, the wireless network 140 can be adjusted to improve network performance when the measured quality of service of the wireless network 140 is less than the expected quality of service. For example, the network parameter may be adjusted in response to determining that the displayed/received frame rate at the display device 102 is less than the acquisition frame rate at the ultrasound imaging device 104. In various embodiments, the network parameter can be adjusted by the display device 102 or the ultrasound imaging device 104.

In some embodiments, adjusting the network parameter may involve switching the wireless network 140 to a different frequency band. For example, the wireless network 140 may be switched from the 2.4 GHz band (e.g., 2.401-2.495 GHz) to the 5 GHz band (e.g., 5.030-4.990 GHz), or vice versa. In some cases, switching from the 2.4 GHz band to the 5 GHz band may allow for greater network speed.

Alternatively, the wireless network 140 may be switched from 5 GHz band to the 2.4 GHz band to allow for greater network range.

Additionally or alternatively, adjusting the network parameter may involve switching the wireless network 140 to a different channel within the same frequency band. For example, the wireless network 140 may be switched to one of the 3 primary non-overlapping channels, 1 (2401-2423 GHz), 6 (2426-2448 GHz), or 11 (2451-2473 GHz), within the 2.4 GHz frequency band. Similarly, the wireless network 140 may be switched amongst one of the 8 primary non-overlapping channels, 36 (5.170-5.190 GHz), 40 (5.190-5.210 GHz), 44 (5.210-5.230 GHz), 48 (5.230-5.250 GHz), 149 (5.735-5.755 GHz), 153 (5.755-5.775 GHz), 157 (5.775-5.795 GHz), or 161 (5.795-5.815 GHz), within the 5 GHz frequency band.

In some embodiments, the wireless network 140 can automatically be switched to the next primary non-overlapping channel. For example, in the 2.4 GHz band, the wireless network 140 may be switched from channel 1 to 6, 6 to 11, or 11 to 1. Similarly, in the 5 GHz band, the wireless network 140 may be switched from channel 36 to 40, 40 to 44, 44 to 48, etc. Additionally or alternatively, a plurality of channels within the frequency band can be scanned to determine the amount of network traffic present on each channel, and the wireless network 140 can be switched to the channel having the least amount of network traffic. For example, a standard channel utilization search may be performed to determine the amount of network traffic present on each channel. Additionally, or alternatively, a DFS (Dynamic Frequency Selection) channel search may be performed to determine the availability of DFS channels that are normally reserved for RADAR and satellite communications. For example, a scan for available DFS channels may be performed in situations where other traditional channels are experiencing high amounts of traffic.

After 314, the method 300 may proceed back to 304 so that additional ultrasound image data can be acquired and transmitted to the display device 102 using the wireless network 140 with the adjusted network parameter.

Figure 4:
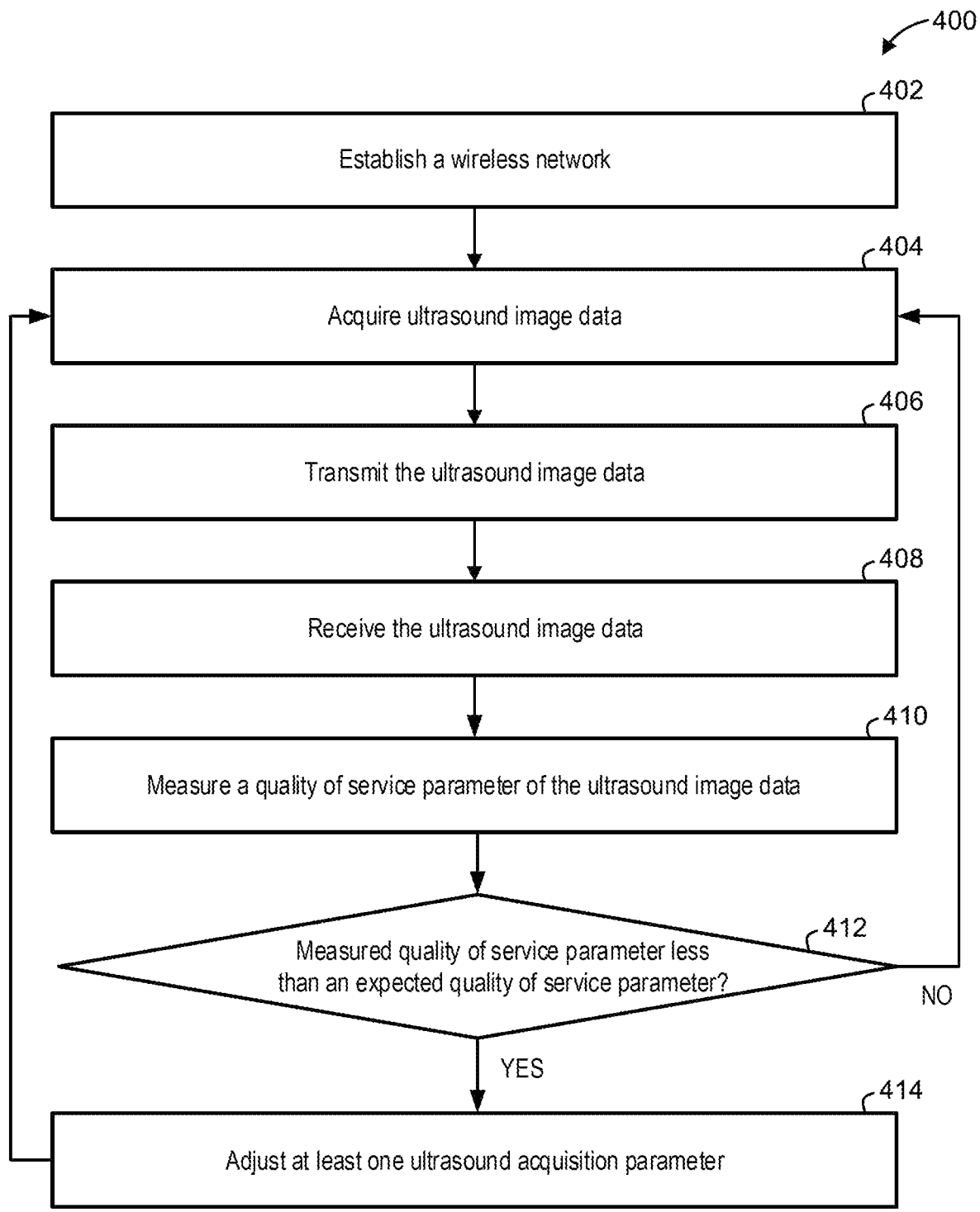
FIG. 4 is a flowchart diagram of another example method for operating the ultrasound imaging system shown in FIGS. 1 and 2, in accordance with at least one embodiment of the present invention.

Referring now to FIG. 4, shown there generally as 400 is a block diagram of another example method for ultrasound imaging, in accordance with at least one embodiment of the present invention. This example implementation of the ultrasound imaging method 400 will now be described with reference to the ultrasound imaging system 100 shown in FIGS. 1 and 2. Acts 402-412 in the method of FIG. 4 generally correspond to acts 302-312 in the method of FIG. 3. However, the action taken after determining that a measured QoS parameter is less than an expected QoS parameter is different between FIGS. 4 and 3 (at acts 414 and 314 respectively).

At 402, the wireless network 140 may be established between the ultrasound imaging device 104 and the display device 102 (e.g., in a similar manner as at 302 of method 300 in FIG. 3). As described herein, the wireless network 140 can be hosted by the ultrasound imaging device 104 or the display device 102, and can be a Wi-Fi™ network that may be initially provisioned using a Bluetooth™ connection.

At 404, the ultrasound imaging device 104 may acquire ultrasound image data using ultrasound acquisition parameters (e.g., in a similar manner as at 304 of method 300 in FIG. 3). As described herein, the ultrasound acquisition parameters may various parameters, including an acquisition frame rate (e.g., a number of frames per second), a sampling frequency (e.g., a number of samples per scan line in each frame), and/or a line density (e.g., a number of scan lines in each frame).

At 406, the ultrasound imaging device 104 may transmit the ultrasound image data to the display device 102 through the wireless network 104 (e.g., in a similar manner as at 306 of method 300 in FIG. 3). As noted above, the ultrasound image data can be transmitted from the ultrasound imaging device 104 to the display device 102 using User Datagram Protocol (UDP), and the ultrasound image data can be transmitted in various formats and include various types of ultrasound data.

At 408, the display device 102 may receive the ultrasound image data from the ultrasound imaging device 104 through the wireless network 140 (e.g., in a similar manner as at 308 of method 300 in FIG. 3).

At 410, the display device 102 may measure a QoS parameter of the received ultrasound image data (e.g., in a similar manner as 310 of method 300 in FIG. 3). As noted, the QoS parameter may include a displayed frame rate (e.g., a number of frames per second of the ultrasound image data displayed at the display device 102) and/or a received frame rate (e.g., a number of frames per second of the ultrasound image data received at the display device 102).

At 412, the display device 102 and/or the ultrasound imaging device 104 may determine whether the measured QoS parameter is less than an expected QoS parameter (e.g., in a similar manner as 312 of method 300 to FIG. 3). As noted, the expected QoS parameter can be an acquisition frame rate at the ultrasound imaging device 104 (e.g., a number of frames per second acquired at the display device 102) and can be determined based on the ultrasound acquisition parameters, such as the acquisition frame rate, sampling frequency, and/or a line density.

As shown in FIG. 4, if the measured QoS parameter is less than the expected QoS parameter (indicating poor network performance in the wireless network 140), the method 400 proceeds to 414. Otherwise, if the measured QoS parameter matches or exceeds the expected QoS parameter, the method 400 proceeds back to 404 and image acquisition continues.

At 414, at least one ultrasound acquisition parameter is adjusted at the ultrasound imaging device 104 to reduce the size of subsequent ultrasound image data acquired by the ultrasound imaging device 104. The ultrasound acquisition parameter may be adjusted in response to determining that the measured QoS parameter is less than the expected QoS parameter at 412. Put another way, the image quality acquired at the ultrasound imaging device 104 can be adjusted to improve network performance when the expected quality of service of the wireless network 140 is less than the measured quality of service. For example, the acquisition frame rate, sampling frequency, and/or line density can be adjusted to reduce the size of subsequent ultrasound image data.

As compared to the method of FIG. 3 (where a network parameter of the wireless network is adjusted to improve network QoS without changing the size or composition of the underlying data), in FIG. 4, an ultrasound acquisition parameter may be adjusted to reduce the size of the data being transmitted. A wireless network 140 with poor QoS may have a lower bandwidth ceiling. With reduced the data size associated with the adjusted ultrasound acquisition parameters, the ultrasound image data stream being received at the display device 102 in a poor wireless network QoS environment may be able to sustain an acceptable bit rate.

Adjusting the ultrasound acquisition parameters at the ultrasound imaging device 104 can modify the quality of the underlying echo data that represents the image tissue (e.g., by decreasing the number of frames per second, the axial resolution, lateral resolution, etc.). However, the modifications to the ultrasound acquisition parameters may be tolerated to improve network performance and improve image data throughput so that an acceptable frame rate of received ultrasound image data is maintained at the display device 102.

This adjustment can generally be made because the ultrasound imaging device 104 incorporates both wireless network connectivity and ultrasound imaging which can have its acquisition parameters modified. This tight coupling allows the ultrasound imaging device 104 to have awareness of both network QoS parameters and ultrasound acquisition parameters in a manner that allows the ultrasound acquisition parameters to be modified in view of the wireless network QoS parameter.

Referring still to FIG. 4, after 414, the method 400 can proceed back to 404 so that additional ultrasound image data can be acquired using the adjusted ultrasound acquisition parameters and transmitted to the display device 102 using the wireless network 140.

Figure 5:
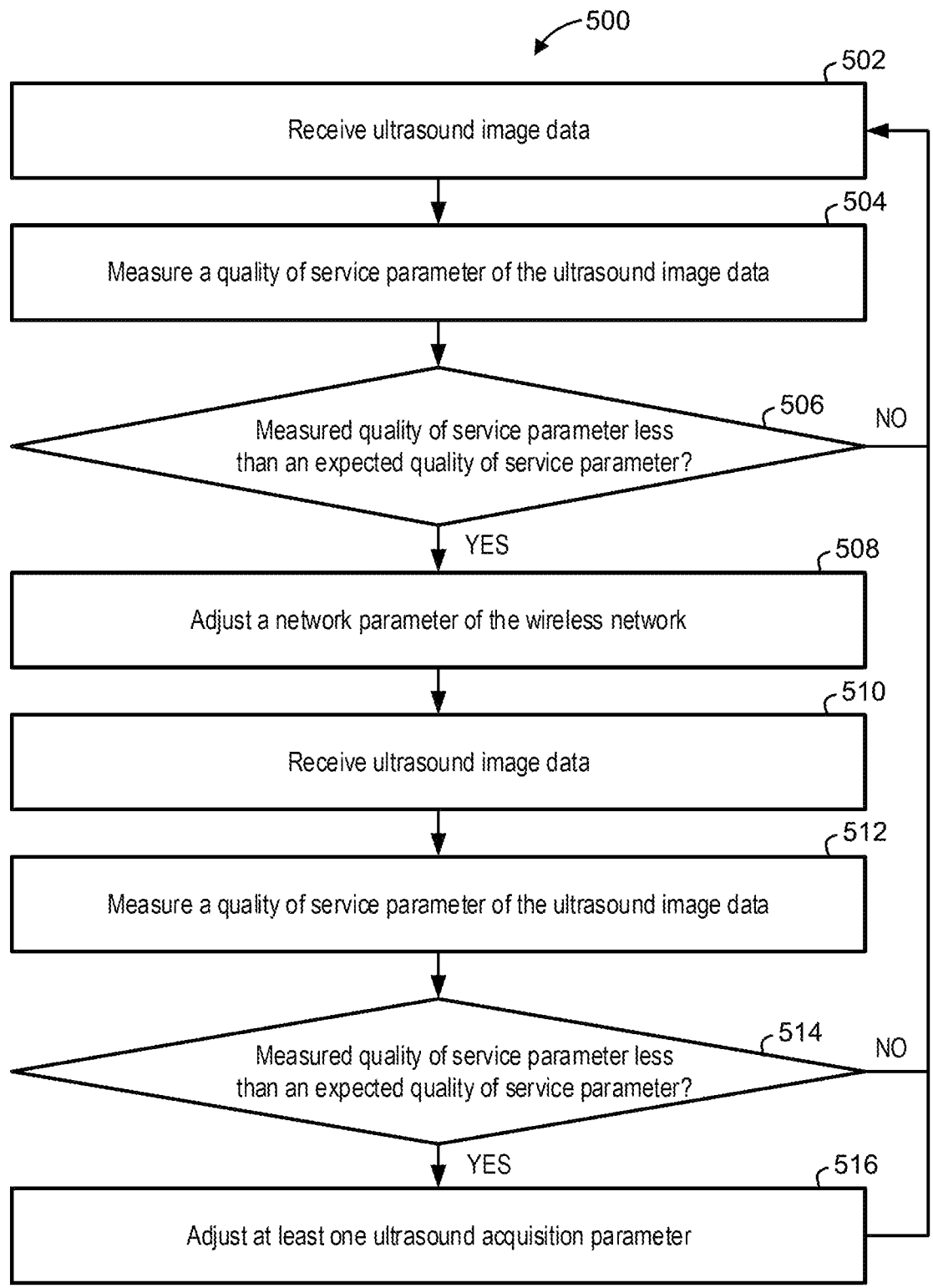
FIG. 5 is a flowchart diagram of another example method for operating the ultrasound imaging system shown in FIGS. 1 and 2, in accordance with at least one embodiment of the present invention.

Referring now to FIG. 5, shown there generally as 500 is a block diagram of another example method for ultrasound imaging, in accordance with at least one embodiment of the present invention. An example implementation of the ultrasound imaging method 500 will now be described with reference to the ultrasound imaging system 100 shown in FIGS. 1 and 2. Some acts in the method of FIG. 5 correspond to acts in FIGS. 4 and 3, except different actions might be taken when a measured QoS parameter is less than an expected QoS parameter. For ease of discussion, the method of FIG. 5 starts with the receiving of ultrasound image data rather than the establishment of a wireless network. However, the acts prior to the receiving of ultrasound image data that were discussed in FIGS. 4 and 3 may also be performed prior to the receiving of ultrasound image data in FIG. 5.

At 502, the display device 102 may receive the ultrasound image data from the ultrasound imaging device 104 through the wireless network 140 (e.g., in a similar manner as at 308 of method 300 and at 408 of method 400).

At 504, the display device 102 may measure a QoS parameter of the received ultrasound image data (e.g., in a similar manner as act 310 of method 300 and at 410 of method 400). As noted, the measured QoS parameter may include a displayed frame rate and/or a received frame rate.

At 506, the display device 102 and/or the ultrasound imaging device 104 may determine whether the measured QoS parameter is less than an expected QoS parameter (e.g., this determination may be performed in a manner similar to 312 of method 300 or 412 of method 400). As noted, the expected QoS parameter can be an acquisition frame rate at the ultrasound imaging device 104 and can be determined based on the ultrasound acquisition parameters, such as the acquisition frame rate, sampling frequency, and/or a line density. The expected QoS parameter can be transmitted from the ultrasound imaging device 104 to the display device 102 so that the display device 102 can make the determination at act 506.

As shown in FIG. 5, if the measured quality of service parameter is less than the expected quality of service parameter, the method 500 proceeds to 508. Otherwise, the network 140 is not experiencing any network performance issues and the method 300 proceeds back to 502 to continue receiving ultrasound imaging data without adjusting any parameters.

At 508, a network parameter of the wireless network 140 is adjusted to reduce network traffic on the wireless network 140 (e.g., in a similar manner as at 314 of method 300). As noted, adjusting the network parameter may involve switching the wireless network 140 to a different frequency band, or switching the wireless network 140 to a different channel within the same frequency band (e.g., automatically, or based on a network traffic scan).

At 510, the display device 102 may receive additional ultrasound image data from the ultrasound imaging device 104 through the wireless network 140 which has the adjusted network parameters.

At 512, the display device 102 may measure a QoS parameter of the additional ultrasound image data received through the adjusted wireless network 140. This may be the same as the QoS parameter measured at act 504, so as to allow for a determination of whether the adjustment of the network parameter at 508 made a difference in the network throughput. As noted above, the measured QoS parameter may include a displayed frame rate and/or a received frame rate.

At 514, the display device 102 and the ultrasound imaging device 104 may again determine whether the measured QoS parameter is less than an expected QoS parameter. This can be performed, for example, in a similar manner to what was performed for act 506 (e.g., to compare the expected QoS parameter of an acquisition frame rate at the ultrasound imaging device 104 with the measured QoS parameter of a received/displayed frame rate at the display device 102). As shown, if the measured QoS parameter is still less than the expected QoS parameter, the method 500 may proceed to 516. Otherwise, it can be determined that the adjustment of the network parameter at 508 resolved network performance issues so that the expected QoS parameter can be attained. As a result, the method 500 can proceed back to 502 to resume receiving ultrasound image data using the wireless network 140 with the adjusted network parameter.

At 516, at least one ultrasound acquisition parameter may be adjusted at the ultrasound imaging device 104 to reduce the size of subsequent ultrasound image data acquired by the ultrasound imaging device 104. This can be performed in a manner similar to act 414 of method 400 shown in FIG. 4. As noted, this may involve adjusting an acquisition frame rate, a sampling frequency, and/or a line density of the ultrasound imaging device 104 so as to reduce the size of subsequent ultrasound image data.

After 516, the method 500 can proceed back to 502 so that further additional ultrasound image data image can be received with the adjusted ultrasound acquisition parameter and over a wireless network 140 with the adjusted network parameter.

As shown, method 500 uses a tiered approach by first adjusting a network parameter at 508, which does not affect the echo data of the imaged tissue. If the quality of service does not improve sufficiently from adjusting the network 140, the ultrasound acquisition parameters can then be adjusted at 516. By modifying the network parameters first, the method 500 attempts to improve poor display performance due to network conditions in a way that preserves as much of the original echo data of the imaged tissue as possible; before resorting to modification of ultrasound acquisition parameters, which may impact image resolution.

Various modifications to the method of FIG. 5 can be made. For example, in some embodiments (not shown), it may be possible that after adjusting a network parameter of the wireless network at 508, the method may revert to act 502 to receive further ultrasound image data and again perform acts 504-508 to determine if the change to the network parameter made a sufficient difference to the network performance. If not, act 508 may modify another network parameter, and the method can again revert to act 502 to further determine whether such changes make a sufficient difference to network performance. This changing of network parameters may continue iteratively while the measured QoS parameter continues to be less than the expected QoS parameter, until all network parameters have been attempted. If the measured QoS parameter still is less than the expected QoS, then the method may proceed to act 510-516 where ultrasound acquisition parameters are modified.

If the measured QoS parameter at 514 still does not meet the expected QoS parameter, an ultrasound acquisition parameter can be modified. After modification of an individual ultrasound acquisition parameter at 516, the method may revert to act 510 to receive additional ultrasound image data with the ultrasound acquisition parameter adjusted. Then acts 512-514 may be performed to determine if the change to the ultrasound acquisition parameter made a sufficient difference to network performance. If not, act 516 may adjust a second ultrasound acquisition parameter, and the method can again revert to act 510 to further determine whether the change to the second ultrasound acquisition parameter made a sufficient difference to network performance. This may continue iteratively while the measured QoS parameter continues to be less than the expected QoS parameter, until adjustment of all ultrasound acquisition parameters have been attempted.

By iteratively changing individual network parameters and then ultrasound acquisition parameters, while testing the network performance after each change, the system can make changes that may improve network performance an incremental manner. Making adjustments in this incremental way may allow for network performance issues to be addressed with fewer adjustments, so that the system an avoid experiencing some of the potential negative impacts of making an adjustment (e.g., potential interrupted connection if changing a network parameter or lower image resolution if changing an ultrasound acquisition parameter).

Figure 6:
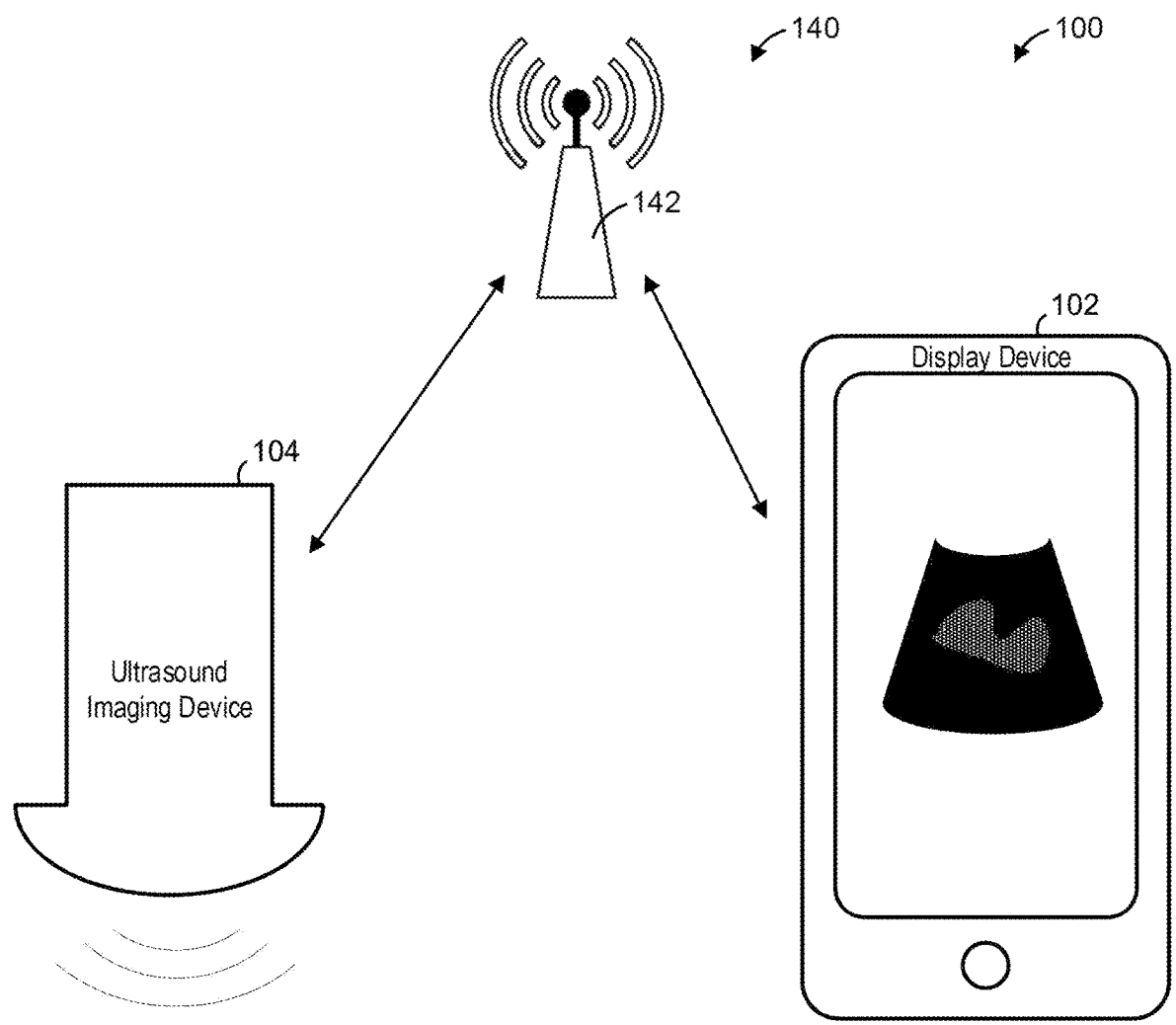
FIG. 6 is a block diagram of an example ultrasound imaging system in another wireless connection configuration, in accordance with at least one embodiment of the present invention.

Referring now to FIG. 6, shown there generally as 600 is a block diagram of another example system for ultrasound imaging, in accordance with at least one embodiment of the present invention. As shown, similar to FIGS. 1 and 2, the ultrasound imaging system 100 includes a display device 102 and an ultrasound imaging device 104. However, in contrast to FIGS. 1 and 2, the ultrasound imaging system 100 further includes a wireless router 142. Router 142 is generally operable to host the wireless network 140 so that communication between the ultrasound imaging device 104 and the display device 102 may be provided through the router 142.

In this configuration, the wireless network 140 is not hosted by the display device 102 or the ultrasound imaging device 104. As a result, the display device 102 and/or the ultrasound imaging device 104 can have access to the Internet through the router 142. However, other traffic on the network, latency, and/or processing limitations of the router 142, may degrade the performance of the wireless network 140. This may degrade the quality of service for transmission of ultrasound image data from the ultrasound imaging device 104 to the display device 102.

Figure 7:
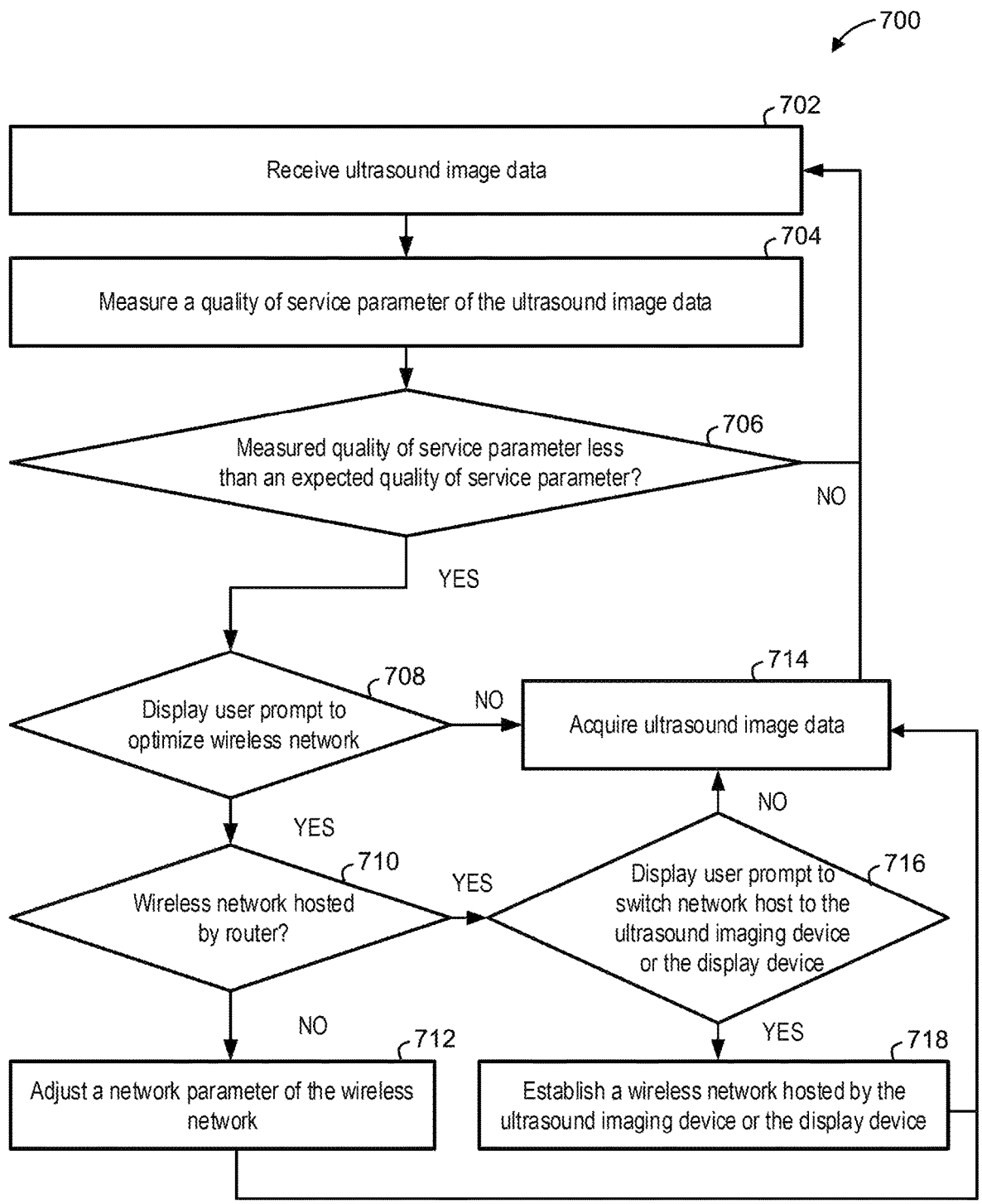
FIG. 7 is a flowchart diagram of an example method of operating the ultrasound imaging system shown in FIG. 6, in accordance with at least one embodiment of the present invention.

Referring now to FIG. 7, shown there generally as 700 is a block diagram of another example method for ultrasound imaging, in accordance with at least one embodiment of the present invention. An example implementation of the ultrasound imaging method 700 will now be described with reference to the ultrasound imaging system 600 shown in FIG. 6, in a scenario where the system 600 suffers from poor network performance as a result of the router 142. Some of the acts of FIG. 7 correspond to acts of FIGS. 3, 4, and 5, and reference will also be made to elements of those figures below.

At 702, the display device 102 may receive the ultrasound image data from the ultrasound imaging device 104 through the wireless network 140 (e.g., in a similar manner as at 308 of method 300, at 408 of method 400, or at 502 and 510 of method 500 described above).

At 704, the display device 102 may measure a QoS parameter of the received ultrasound image data (e.g., in a similar manner as 310 of method 300, at 410 of method 400, or at 504 and 512 of method 500). As described herein, the QoS parameter may include a displayed frame rate and/or a received frame rate.

At 706, at least one of the display device 102 and the ultrasound imaging device 104 may determine whether the measured QoS parameter is less than an expected QoS parameter. For example, this may be performed in a manner similar to act 312 of method 300, act 412 of method 400, or act 506 and 514 of method 500). As described herein, the expected QoS parameter can be an acquisition frame rate at the ultrasound imaging device 104 (e.g., a number of frames per second acquired at the display device 102) and can be determined based on the ultrasound acquisition parameters, such as the acquisition frame rate, sampling frequency, and/or a line density. If the measured QoS parameter meets or exceeds the expected QoS parameter (the 'NO' branch at 706), then it is determined that the wireless network 140 is operating as expected and the method may revert back to 702 so that image acquisition may continue as per normal and ultrasound image data may be received at the display device 102. If the measured QoS parameter is less than the expected QoS parameter, then method may proceed to act 708.

At 708, a user prompt may be displayed at the display device 102 offering to optimize the wireless network 140. For example, the user prompt can be displayed using a graphical user interface at the display device 102. As shown, if the user accepts the offer to optimize the wireless network, the method 700 proceeds to 710. Otherwise, the method 700 proceeds to 714.

At 710, it is determined whether the wireless network 140 is hosted by the router 142. As shown, if the wireless network 140 is hosted by the router 142, the method 700 proceeds to 716. Otherwise, the method 700 proceeds to 712.

At 712, a network parameter of the wireless network 140 may be adjusted to reduce network traffic on the wireless network 140 (e.g., in a similar manner as at 314 of method 300 and at 508 of method 500). As described herein, adjusting the network parameter may involve switching the wireless network 140 to a different frequency band, or switching the wireless network 140 to a different channel within the same frequency band (e.g., automatically, or based on a network traffic scan).

At 716 (e.g., if the wireless network is hosted by the router 142), a user prompt is displayed at the display device 102 offering to switch the host of the wireless network 140 to the ultrasound imaging device 104 or the display device 102 (e.g., so that resulting connection would be configured similar to as shown in FIG. 1). For example, the user prompt can be displayed using a graphical user interface of the display device 102.

At 718 (e.g., if the user responds 'yes' to the prompt at 716), the wireless network 140 is established between the ultrasound imaging device 104 and the display device 102 (e.g., in a similar manner as at 302 of method 300 and at 402 of method 400) that is hosted by either the ultrasound imaging device 104 or the display device 102. As described herein, the established wireless network 140 can be a Wi-Fi™ network that may be initially provisioned using a Bluetooth™ connection.

At 714, the ultrasound imaging device 104 may acquire additional ultrasound image data and transmit the ultrasound image data to the display device 102 through the wireless network 140 (e.g., in a similar manner as at 304 and 306 of method 300, and at 404 and 406 of method 400). After 714, the method 700 can proceed back to 702 so that further additional ultrasound image data can be received.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (e.g., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

What is claimed is:

1. A method for ultrasound imaging, the method comprising:
    establishing a wireless network between an ultrasound imaging device and a display device;
    acquiring ultrasound image data at the ultrasound imaging device using ultrasound acquisition parameters;
    transmitting the ultrasound image data from the ultrasound imaging device to the display device over the wireless network;
    receiving the ultrasound image data at the display device;
    measuring, at the display device, a quality of service parameter of the received ultrasound image data;
    determining, at at least one of the display device or the ultrasound imaging device, whether the measured quality of service parameter is less than an expected quality of service parameter, the expected quality of service parameter being determined based on the ultrasound acquisition parameters used to acquire the ultrasound image data at the ultrasound imaging device; and
    in response to determining that the measured quality of service parameter is less than the expected quality of service parameter, adjusting a network parameter of the wireless network to reduce network traffic on the wireless network by at least one of the following steps:
    i) switching the wireless network to a different band or
    ii) switching the wireless network to a different channel within the same frequency band which comprises scanning a plurality of channels within the frequency band to determine an amount of network traffic present on each channel and switching the wireless network to the channel having the least amount of network traffic.

2. The method of claim 1, wherein the measured quality of service parameter comprises a displayed frame rate of the received ultrasound image data, and the expected quality of service parameter comprises an acquisition frame rate at the ultrasound imaging device.

3. The method of claim 1, wherein in response to the determining that the measured quality of service parameter is less than the expected quality of service parameter, the method further comprises adjusting at least one ultrasound acquisition parameter of the ultrasound acquisition parameters used at the ultrasound imaging device, the adjusting being performed to reduce the data size of subsequent ultrasound image data acquired by the ultrasound imaging device.

4. The method of claim 3, wherein the adjusted at least one ultrasound acquisition parameter comprises: acquisition frame rate, sampling rate, line density or sampling frequency.

5. The method of claim 1, wherein prior to the determining whether the measured quality of service parameter is less than the expected quality of service parameter, the method further comprises:
determining the expected quality of service parameter at the ultrasound imaging device; and
transmitting the expected quality of service parameter from the ultrasound imaging device to the display device.

6. The method of claim 1, wherein the wireless network is hosted by the ultrasound imaging device, and the method further comprises transmitting the measured quality of service parameter from the display device to the ultrasound imaging device over the wireless network.

7. The method of claim 6, wherein:
the ultrasound image data is transmitted over the wireless network using a first communication protocol; and
the measured quality of service parameter is transmitted over the wireless network using a second communication protocol that is different from the first communication protocol.

8. The method of claim 7, wherein the first communication protocol comprises User Datagram Protocol (UDP) and the second communication protocol comprise Transmission Control Protocol (TCP).

9. A system for ultrasound imaging, the system comprising:
an ultrasound imaging device configured to acquire ultrasound image data using ultrasound acquisition parameters; and
a display device in electronic communication with the ultrasound imaging device over a wireless network, the display device configured to:
receive the ultrasound image data from the ultrasound imaging device over the wireless network; and
measure a quality of service parameter of the received ultrasound image data;
wherein at least one of the display device or the ultrasound imaging device is configured to:
determine whether the measured quality of service parameter is less than an expected quality of service parameter, the expected quality of service parameter being determined based on the ultrasound acquisition parameters used to acquire the ultrasound image data at the ultrasound imaging device; and
in response to determining that the measured quality of service parameter is less than the expected quality of service parameter, adjusting a network parameter of the wireless network to reduce network traffic on the wireless network by at least one of the following steps: i) switching the wireless network to a different band or ii) switching the wireless network to a different channel within the same frequency band which comprises scanning a plurality of channels within the frequency band to determine an amount of network traffic present on each channel and switching the wireless network to the channel having the least amount of network traffic.

10. The system of claim 9, wherein the measured quality of service parameter comprises a displayed frame rate of the received ultrasound image data, and the expected quality of service parameter comprises an acquisition frame rate at the ultrasound imaging device.

11. The system of claim 9, wherein at least one of the display device and the ultrasound imaging device is further configured to: in response to the determining that the measured quality of service parameter is less than the expected quality of service parameter, adjust at least one ultrasound acquisition parameter of the ultrasound acquisition parameters used at the ultrasound imaging device, the adjusting being performed to reduce the data size of subsequent ultrasound image data acquired by the ultrasound imaging device.

12. The system of claim 11, wherein the adjusted at least one ultrasound acquisition parameter comprises: acquisition frame rate, sampling rate, line density or sampling frequency.

13. The system of claim 9, wherein the ultrasound imaging device is further configured to: prior to the determining whether the measured quality of service parameter is less than the expected quality of service parameter,
determine the expected quality of service parameter; and
transmit the expected quality of service parameter to the display device.

14. The system of claim 9, wherein the wireless network is hosted by the ultrasound imaging device, and the display device is further configured to: transmit the measured quality of service parameter to the ultrasound imaging device over the wireless network.

15. The system of claim 14, wherein:
the ultrasound image data is transmitted over the wireless network using a first communication protocol; and
the measured quality of service parameter is transmitted over the wireless network using a second communication protocol that is different from the first communication protocol.

16. The system of claim 15, wherein the first communication protocol comprises User Datagram Protocol (UDP) and the second communication protocol comprise Transmission Control Protocol (TCP).

* * * * *